(12) United States Patent
Gennari et al.

(10) Patent No.: US 9,381,204 B2
(45) Date of Patent: Jul. 5, 2016

(54) PHARMACEUTICAL COMPOSITIONS CONTAINING PHOSPHATIDYLSERINE AND CURCUMIN

(71) Applicant: FIDIA FARMACEUTICI S.P.A., Abano Terme (IT)

(72) Inventors: Giovanni Gennari, Abano Terme (IT); Susi Panfilo, Abano Terme (IT)

(73) Assignee: FIDIA FARMACEUTICI S.P.A., Abano Terme (IT)

( * ) Notice: Subject to any disclaimer, the term of this patent is extended or adjusted under 35 U.S.C. 154(b) by 0 days.

(21) Appl. No.: 14/374,236

(22) PCT Filed: Jan. 23, 2013

(86) PCT No.: PCT/IB2013/050579
§ 371 (c)(1),
(2) Date: Jul. 24, 2014

(87) PCT Pub. No.: WO2013/111066
PCT Pub. Date: Aug. 1, 2013

(65) Prior Publication Data
US 2015/0038467 A1  Feb. 5, 2015

(30) Foreign Application Priority Data
Jan. 26, 2012 (IT) .............................. PD2012A0021

(51) Int. Cl.
A61K 31/66 (2006.01)
A61K 31/685 (2006.01)
A61K 45/06 (2006.01)
A61K 31/12 (2006.01)

(52) U.S. Cl.
CPC ............... *A61K 31/685* (2013.01); *A61K 31/12* (2013.01); *A61K 45/06* (2013.01)

(58) Field of Classification Search
CPC .................................................... A61K 31/131
USPC ......................................................... 514/114
See application file for complete search history.

(56) References Cited

U.S. PATENT DOCUMENTS

| 6,733,797 B1 | 5/2004 | Summers |
| 2007/0082065 A1 | 4/2007 | Krawitz |
| 2011/0229555 A1 | 9/2011 | Helson et al. |
| 2012/0003378 A1 | 1/2012 | Howard |

FOREIGN PATENT DOCUMENTS

| EP | 2 228 062 A1 | 9/2010 |
| EP | 2 229 940 A1 | 9/2010 |
| WO | WO 2007/101551 A2 | 9/2007 |

*Primary Examiner* — Raymond Henley, III
(74) *Attorney, Agent, or Firm* — Birch, Stewart, Kolasch & Birch, LLP (57) ABSTRACT

The present invention describes and claims stable pharmaceutical compositions and/or food supplements based on phosphatidylserine (PS) and curcumin, which are consequently devoid of degradation products, for use in the prevention and treatment of disorders associated with brain aging, and in the prevention and treatment of osteoporosis and/or osteoarthritis.

36 Claims, 6 Drawing Sheets

PHARMACEUTICAL COMPOSITIONS CONTAINING PHOSPHATIDYLSERINE AND CURCUMIN

CROSS REFERENCE TO RELATED APPLICATIONS

This application is the National Phase of PCT International Application No. PCT/IB2013/050579, filed on Jan. 23, 2013, which claims priority under 35 U.S.C. 119(a) to Patent Application No. PD2012A000021, filed in Italy on Jan. 26, 2012, all of which are hereby expressly incorporated by reference into the present application.

SUBJECT OF THE INVENTION

The present invention describes and claims stable pharmaceutical compositions and/or food supplements based on phosphatidylserine (PS) and curcumin, which are consequently devoid of degradation products, for use in the prevention and treatment of disorders associated with brain aging, and in the prevention and treatment of osteoporosis and/or osteoarthritis.

FIELD OF INVENTION

The functional decline of the central nervous system (CNS) that takes place during the physiological process of brain aging often causes a deterioration in the cognitive functions of elderly people, which can take the form of behavioural disorders with alterations of the temporal and spatial memory.

This functional decline is associated with biochemical and structural alterations of the lipid composition of the neuronal membranes, and with reduced brain enzyme activity, which can lead to a reduction in the synaptic density.

As phosphatidylserine (PS) is the major acid phospholipid in the brain, scientific research has long been seeking a pharmacological treatment for age-related cognitive disorders consisting of phospholipids which can prevent (and/or partly reconstruct) this structural and functional deficiency of the aging neuronal membranes.

Pre-clinical and clinical studies conducted in humans have demonstrated that especially in elderly people, oral administration of PS can elicit a significant increase in learning capacity and temporal and spatial memory, even in the case of particularly incapacitating disorders like senile dementia and Alzheimer's disease (Cenacchi T. et al.; Aging Clin Exp Res; 1993; 5:123-133; Nunzi M G et al.; Adv Exp Med Biol; 1992; 318:393-8).

The physiological and pathological deterioration of the cognitive functions of elderly people can often be associated with a hormonal reduction due to the normal decline in endocrine functionality (such as the menopause or andropause), or to sudden termination of the production of certain hormones due to surgical removal of the secreting organ (such as partial or total ovariectomy). This situation is often followed by other disorders such as osteoporosis.

The term "osteoporosis" means a condition whereby the skeleton is at greater risk of fractures due to a reduction in mass and modification of the bone microarchitecture. Osteoporosis is defined as over 30% bone loss. It mainly occurs in trabecular bone, which is subject to the largest number of fractures, and starts with a reduction in the calcium tone of the bone mass (osteopenia). The bones most often affected by a reduction in calcium tone are the dorsolumbar vertebrae, the femur and the wrist. As osteopenia progresses, a vertebral collapse or fracture of the neck of the femur may occur.

Osteoporosis is classified as primary (original) or secondary, ie. resulting from a correlated event; however, the primary form accounts for nearly all cases (95%).

Primary osteoporosis comprises post-menopausal osteoporosis and senile osteoporosis (the latter being due to various causes, including immobility and a low intake of calcium, magnesium, vitamin D and other important micronutrients).

Secondary osteoporosis can be classified as caused by lengthy immobilisation, rheumatoid arthritis, malignant tumours, or reduced intestinal absorption of nutrients.

It is the most widespread of the various bone disorders, affecting both sexes, but mainly post-menopausal women; in the USA, the majority of adults over 50 years old suffer from osteoporosis or low bone density.

The cause is an imbalance between osteoblasts and osteoclasts; the first category of cells contributes to bone formation, while the second contributes to bone resorption, so if the osteoclasts work more rapidly than the osteoblasts, the bone deteriorates. During the menopause, osteoclast production increases due to loss of oestrogens, which leads to an increase in cytokines correlated with osteoclast production. In the second form, osteoblast activity declines with age.

The available preventive and curative treatments include:
administration of cholecalciferol to promote intestinal absorption of calcium,
calcium and magnesium supplementation,
administration of diphosphonates which inhibit osteoclast activity,
hormone replacement therapy with oestrogen and progestogens for menopausal women and with testosterone for men,
osteoclast inhibition with calcitonin,
clodronate with subcutaneous calcitonin for the treatment of fracture pain.

Osteoarthritis (OA) is often associated with osteoporosis in the elderly; this highly disabling disorder is characterised by progressive erosion of the joint cartilage due to degradation of joint matrix and loss of cell components. The physiological aging process of the joint surfaces seems to involve the enzymatic mechanisms of OA.

It is known that the mechanical imbalance which can involve the joint as a whole can trigger onset of said disorder.

This joint instability can be substantially caused by different factors (such as trauma, inflammation of the joint system, cartilage erosion, incorrect gait or posture), and can lead to an alteration of the delicate balance between synthesis and degradation of the extracellular matrix, which is mainly synthesised by the chondrocytes and synoviocytes.

When this situation of perfect but delicate homeostasis is disrupted, degradation of the matrix exceeds its synthesis and a slow but progressive degradation process begins, which is poorly compensated by the corresponding synthesis process, as a result of the loss of chondrocytes.

Excessive and/or incorrect joint loading can cause a chondrocyte response expressed by synthesis of the enzymes responsible for cartilage degradation. The protease enzymes responsible for cartilage degradation are called matrix metalloproteases (MMP), and are synthesised by chondrocytes when they are stimulated by inflammatory cytokines such as IL-1 and TNF-α, which are produced and released in the joint cavity, especially at the onset of an inflammatory disorder. IL-1 stimulates the synthesis of high levels of nitric oxide (responsible for the death by apoptosis of the chondrocytes), and also inhibits the synthesis of proteoglycans (components of matrix) by the chondrocytes (Dozin B. et al., Matrix Biology, 2002, 21:449-459).

The available curative treatments include the administration of steroidal and non-steroidal medicaments in association with intra-articular viscosupplementation injections.

Pharmaceutical compositions containing antioxidants such as curcumin are currently marketed as a preventive and curative treatment for the above-mentioned neurodegenerative disorders and inflammatory disorders in general.

Curcumin (diferuloylmethane; 1,7-bis[4-hydroxy-3-methoxyphenyl]-1,6-heptadiene-3,5-dione) is a liposoluble molecule and, together with its mono- and dimethoxy derivatives known as curcuminoids, is obtained by extraction with solvent from the dried and ground rhizome of the *Curcuma longa* (turmeric) plant. Turmeric was historically used in Indian Ayurvedic medicine to treat a wide variety of disorders, but it was not until the 20th century that scientific research identified curcumin as the factor responsible for most of its biological activity. Curcumin has formed the subject of numerous preclinical and clinical studies, so its anti-inflammatory and antioxidant power is well documented: it possesses the ability to regulate the oxidative balance of the cells, intervening in numerous mechanisms in different ways; in particular, it inhibits a series of factors with strongly inflammatory activity (COX 1 and 2, TNF, lipoxygenase and interferon-gamma). Finally, its efficacy as an antitumoral has been demonstrated in vitro (Bengmark S., JPEN, 2006, 30(1):45-51).

However, its clinical use is limited by its very low bioavailability after oral administration, due to the low gastrointestinal absorption caused by the lipophilicity of said active ingredient. For these reasons, many attempts have been made to increase the bioavailability of curcumin, such as combining it with piperine (which is toxic) or with other *Curcuma longa* oils (U.S. Pat. No. 7,736,679), or encapsulating it in liposomes or phytosomes consisting of phospholipids/lecithin (EP1991244).

However, the oral availability of curcumin remains limited.

Phosphatidylserine is an acid phospholipid with three ionisable groups (amino, phosphate, and carboxyl) which is mainly present in the inner part of the plasma membrane; numerous studies have demonstrated its efficacy in facilitating neuronal activities that depend on the cell membrane, and in normalising the density of the neuronal receptors to restore the correct levels of acetylcholine and dopamine.

The PS currently on the market is based on production and purification processes (known to the skilled person) involving enzymatic conversion of phosphatidylcholine (PC) and/or phosphatidylethanolamine (PE) to PS through a transphosphatidylation reaction catalysed by the enzyme phospholipase D (PLD), with subsequent purification by final extraction with organic solvents.

PS is produced as a powder but mainly sold in fluid form, generally mixed with oily solvents containing triglycerides for its formulation as soft capsules.

However, this phospholipid presents considerable problems of formulation stability for three main reasons:

the presence of traces of PLD enzyme in the final composition of soft capsules which leads to rapid decomposition of PS followed by the formation of phosphatidic acid (PA) and/or phosphatidylglycerol, due to the replacement of serine with the glycerol present in the capsule (EP1663157);

in the presence of free radicals (ROS), PS can undergo a process of lipid peroxidation of the polyunsaturated fatty acids of the molecule (Bochkov V., Antioxidants & Redox Signaling; 2010, 12(8):1009-1058);

finally, PS can also undergo the oxidative process of its polar head, serine, which leads to accumulation of PA (Maciel E. et al., J Am Soc Mass Spectrom, 2011, 22(10):1804-14).

The subject of the present invention is a novel pharmaceutical composition containing a combination of PS and curcumin, because the Applicant has discovered that it stabilises said phospholipid by slowing and/or arresting its multiple breakdown and oxidation processes (previously described), thus allowing the formulation of a stable PS/curcumin combination devoid of degradation products to prepare pharmaceutical compositions (and supplements) in all pharmaceutical and non-pharmaceutical forms currently known to the skilled person (capsules, bars, solutions/dispersions for vial preparation).

DETAILED DESCRIPTION OF THE INVENTION

The present invention describes and claims novel pharmaceutical compositions or diet supplements based on PS and curcumin for use in the prevention and treatment of the disorders associated with brain aging described above, and the prevention and treatment of osteoporosis and/or osteoarthritis.

The Applicant has discovered that the combination of curcumin with phosphatidylserine stabilises said phospholipid in such a way that pharmaceutical compositions (or other formulations) containing said combination do not present PS in degraded/oxidised form, or even the degradation products of PS described above, thus maintaining all the pharmacological properties of PS unchanged. The Applicant has also described novel pharmaceutical forms such as soft capsules or tablets, solutions and/or dispersions, bars or other formulations known to the skilled person, containing the novel stable combination consisting of PS/curcumin.

The subject of the present invention is novel therapeutic uses of pharmaceutical compositions containing PS and curcumin:

use in the prevention and treatment of neurodegenerative disorders with a decline in cognitive aspects and memory alterations, such as Alzheimer's disease, senile and pre-senile dementia, and vascular dementia;

use in the prevention and treatment of primary and secondary osteoporosis;

use in the prevention and treatment of osteoarthritis (OA).

The Applicant has demonstrated the synergic effect of the novel stable PS/curcumin combination in reducing nitric oxide (NO) production.

These results are extremely important, because NO is involved in the pathogenesis of:

the oxidative cell damage which occurs, for example, in reperfusion after ischaemia;

neurodegenerative disorders such as Alzheimer's disease, senile and pre-senile dementia, and vascular dementia;

disorders of the bone structure and joints, such as osteoporosis and osteoarthritis.

In the CNS, pathogens, stress conditions, age or neurodegenerative disorders can trigger an inflammatory response driven by activation of the glial cells (in particular the microglial cells) which, by secreting pro-inflammatory molecules, neurotransmitters and reactive species such as NO, modulate said inflammatory processes. In particular, high concentrations of NO have been found in the neurones and glia where it contributes to the maintenance and progression of the neuroinflammatory process due to its particular ability to create free radicals that prejudice the integrity of the cell by subjecting it to oxidative stress (Fernandez A P et al., Curr Pharm Des, 2010, 16(25):2837-50). In addition, NO also appears to be involved in the bone development processes by increasing osteoclast differentiation, thus compromising the bone mineral density (Ninomiya J T, Poster Session-Bone Cell Biology, 2001, 47th AM of Orthopaedic Research Society, California). Finally, the presence and active role of NO in the joint tissue of patients suffering from OA has been demonstrated: a high concentration of NO inhibits the mitochondrial activity of the chondrocytes and synoviocytes and causes the formation of free radicals and consequently cell death.

The inflammatory species strongly involved in the processes described include cytokines, especially interleukins. They are produced by activated macrophages, and are responsible for a series of cell activities, including apoptosis. In particular, it has been demonstrated that in the cells of the nervous system, interleukins are involved in the inflammatory cascade that influences the development and course of degenerative disorders such as Alzheimer's disease (Kitazawa et al., J Immunol, 2011, 187, 6539-6549).

The role of PS in inhibiting the enzyme responsible for NO synthesis and the consequent slowing of the osteoclastogenesis process that causes loss of trabecular bone is well known (Aramaki Y, Biochem Biophys Res Commun, 2001, 280(4): 982-7).

Finally, the ability of curcumin to inhibit NO production by regulating the enzyme NO synthetase is also known; due to its anti-inflammatory capacity, curcumin has therefore been tested in neurodegenerative disorders, OA and prevention of bone deterioration (Kim W K, j Cell Biochem, 2011, 112(11): 3159-66).

The Applicant has now surprisingly discovered, and subsequently demonstrated, the synergic effect of the novel stable PS/curcumin combination in reducing nitric oxide (NO) production in the microglia cells after stimulation with pro-inflammatory agents (LPS).

This result was wholly unexpected, and in view of the known implications of NO described above, supports the novel therapeutic uses of the pharmaceutical composition containing the stable PS/curcumin combination in both neurodegenerative disorders and those involving the bone apparatus.

The subject of the present invention is therefore novel uses and methods of treating the following disorders, involving daily administration of 1 or more pharmacologically active doses of the pharmaceutical composition based on PS/curcumin:

prevention and treatment of neurodegenerative disorders involving a reduction in cognitive aspects and memory alterations, such as Alzheimer's disease, senile and pre-senile dementia, and vascular dementia;

prevention and treatment of primary and secondary osteoporosis;

prevention and treatment of osteoarthritis (OA).

The PS usable in the combination described is produced due to the PLD enzyme which catalyses the transphosphatidylation between PC and serine, a reaction that can take place in an aqueous environment (EP1231213, EP1048738) or a biphasic water/solvent system (EP0776976, EP1890706). However, it is preferable to use a PS produced according to patent EP1890706, wherein PS can be produced in the presence of a bivalent metal oxide in a water-alcohol reaction environment, or in an environment containing an aprotic solvent, or a biphasic system; the preparation of PS in a biphasic system formed by an aqueous solution and an a organic solvent in the presence of calcium oxide is even more preferable, because this system allows the preparation of a PS with a high concentration and a high degree of purity.

The curcumin (with the derivatives thereof, such as its esters which act as prodrugs) usable in this invention can be acquired as such (generally associated with other curcuminoids present in smaller proportions, such as Curcumin Complex), or as Biocurcumin (BCM-95®) associated with oils and polymers that increase its bioavailability (US20070148263), or formulated in combination with piperine (Shobha et al., Planta Med, 1998, 64: 353-56), or obtained as micro- or nanoemulsions/nanodispersions that use lecithin and/or fatty acids and/or triglycerides and optionally also surfactants, such as Tween 80, to stabilise the molecule and make it more bioavailable.

The novel stable combination forming the subject of the present invention consists of:

PS (preferably as sodium salt) in the concentration of 50 to 400 mg per dose of pharmaceutical composition, preferably 100 to 200 mg;

curcumin at the concentration of 50 to 1000 mg per dose of active ingredient, preferably 100 to 600 mg, depending on the initial composition of the active ingredient used in combination with PS.

The preferred pharmaceutical (and non-pharmaceutical) forms are soft capsules, sachets, tablets, bars or solutions/dispersions for vial preparation.

The particularly preferred pharmaceutical forms are soft capsules and sachets; the combination of PS and curcumin can be formulated in compositions prepared as known to the skilled person using, for example, lipid excipients (such as fatty acids, triglycerides and/or phospholipids); surfactants (such as polysorbates); adsorbent agents (such as sorbitol and mannitol); preservatives/antioxidants (such as ascorbic acid); pH regulators (such as citric acid); and finally, the novel compositions according to the invention can also contain pharmacologically/biologically active agents of natural and/or synthetic origin such as vitamins, mineral salts, tonic agents (such as ginseng and ginkgo-biloba), anti-inflammatories and aminoacids.

Some examples of formulation of the novel combination of PS and curcumin according to the invention are set out below by way of example but not of limitation, together with the results of the in vitro study.

EXAMPLE 1

Preparation of Sachets Containing 200 mg PS/400 mg Curcumin

Ingredients

| | |
|---|---|
| PS sodium salt | 200 mg |
| Curcumin (95%) | 400 mg |
| Aspartame | 10 mg |
| Colloidal silicon dioxide | 20 mg |
| Soya lecithin | 20 mg |
| Natural lemon flavouring | 60 mg |
| Mannitol | 200 mg |
| Fructose q.s. for | 6000 mg |

The sachets must contain a uniform, flowable granulate which is pleasant to take and stable over time.

Silica makes the granulate flowable and prevents the formation of aggregates; mannitol and lecithin facilitate the dispersion of the active ingredient in water, while fructose, preferably with a particle size of less than 150 μm, allows the preparation of a uniform mixture of PS/curcumin with the excipients.

Preparation Process: Mixing of Ingredients

The PS, pre-mixed with suitably sieved lecithin and with curcumin, is loaded into a cube mixer, and all the remaining excipients are then added after sieving.

The atmosphere is rendered inert with a filtered nitrogen flow, and mixing proceeds for 30 minutes.

The mixture is then used to fill sachets (again under nitrogen flow) which are heat-sealed.

EXAMPLE 2

Preparation of Soft Capsules Containing 100 Mg PS/200 Mg Curcumin

Ingredients

| | |
|---|---|
| PS sodium salt | 100 mg |
| Curcumin (95%) | 200 mg |
| Lecithin | 50 mg |
| Vegetable oil | 300 mg |

Ingredients of Shell

| | |
|---|---|
| Gelatin | 360 mg |
| Glycerol | 140 mg |
| Brown iron oxide E172 | 3 mg |
| Red iron oxide E172 | 1.2 mg |
| Sodium ethyl p-hydroxybenzoate | 1.6 mg |
| Sodium propyl p-hydroxybenzoate | 0.9 mg |

Preparation Process: Mixing of Ingredients

The FRYNA VME 400 turboemulsifier is used for this procedure; the described quantity of vegetable oil is first poured into it, and heated to a homogenous temperature of 25° C.

Half the total quantity of PS, curcumin and the remaining ingredients are added;

the apparatus is closed and a vacuum created; the turbine is then operated for 15 minutes. The second half of the ingredients is added, and the vacuum created again. The turbine is operated for a further 40 minutes. The temperature must not exceed 40° C.

The homogenising mill is then also activated for a total of 90 minutes until the active constituents and the remaining ingredients are fully and evenly dispersed.

The mill is shut down, while the turbine remains in operation for a further 10 minutes.

The mixture obtained is then used to fill capsules.

EXAMPLE 3

PS/Curcumin: Synergic Inhibition of NO Production

This experiment was conducted to evaluate the ability of the stable PS/curcumin combination to modulate the activation of the microglia in vitro compared with the effect generated by PS alone and curcumin alone.

Materials and Methods

PS (sodium salt), produced and purified according to EP1890706 (example 3), was resuspended in 2:1 chloroform/methanol, dried by evaporation and resuspended in PBS at the final concentration of 100 μM. 95% pure curcumin, prepared in DMSO at the final active ingredient concentration of 20 mM, was used for this experiment.

Experimental Model

An in vitro glial activation model using the murine microglia BV-2 cell line was selected for this experiment:

50,000 cells/well were initially seeded in 96-well plates and cultured in DMEM containing 10% FCS, glutamine and antibiotics at 37° C. If activated with LPS (lipopolysaccharide, an endotoxin of Gram-negative bacterial, normally used as pro-inflammatory stimulus both in vitro and in vivo), these cells release NO into the culture medium; the experiment therefore involved stimulating them with 0.1 μg/ml LPS overnight in the presence or absence of PS (10 and 30 μM) or curcumin (2.5 and 5 μM) at different concentrations.

Finally, to evaluate the synergy between the two active constituents, the PS/curcumin combination was tested in the presence of LPS 0.1 μg/ml (as described above):

10 μM PS+2.5 μM curcumin, and

10 μM PS+5 μM curcumin.

The final NO content in the medium was measured with the Griess test: briefly, aliquots of medium were mixed with equal volumes of Griess reagent (0.1% N(1-naphthyl)ethylenediamine dihydrochloride, 1% sulphanylamide and 0.4M HCl). After 15 minutes' reaction, the absorbance was measured at 570 nm.

Results

Figure 1:
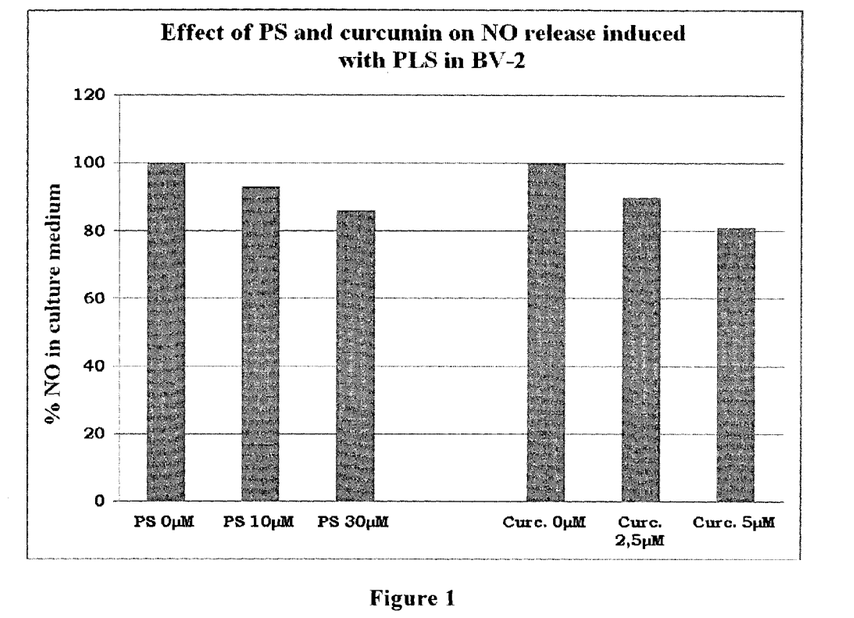
FIG. 1 is a graph showing the effect caused by PS and by curcumin on the release of NO into the culture medium by the murine microglia BV-2 cells.

FIG. 1 shows the effect caused by PS and by curcumin (at the above-mentioned concentrations) on the release of NO into the culture medium by the murine microglia BV-2 cells: both molecules inhibit the release of NO into the medium in a dose-dependent manner, so both PS and curcumin reduce NO production in cells activated by LPS, thus confirming their anti-inflammatory power described in the literature and previously mentioned.

Figure 2:
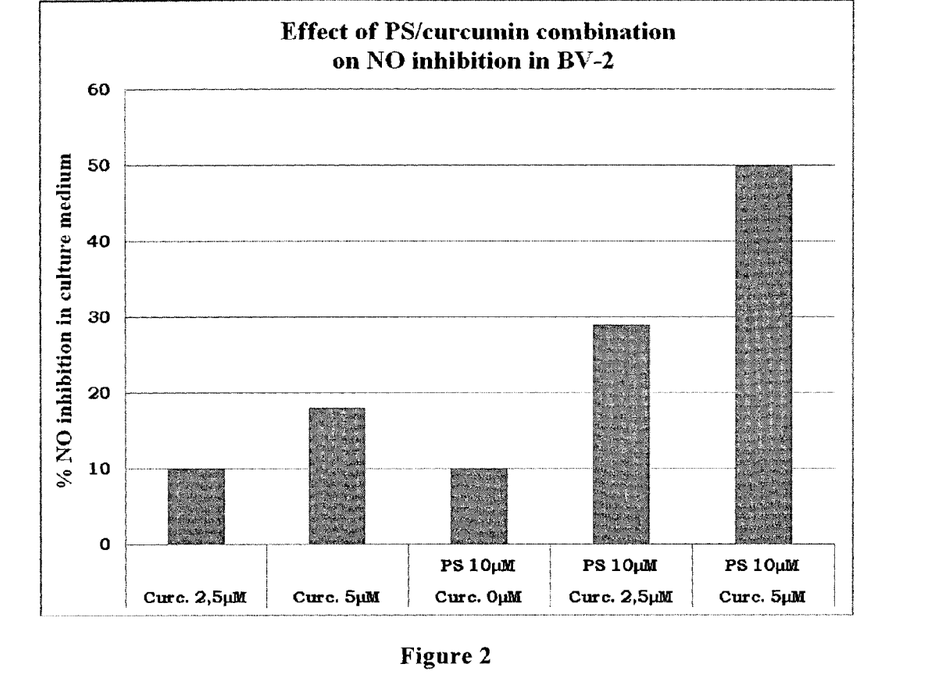
FIG. 2 is a graph demonstrating the synergic effect elicited by the stable novel PS/curcumin combination in inhibiting the release of NO by the activated microglia.

FIG. 2 clearly and unequivocally demonstrates the synergic effect elicited by the stable novel PS/curcumin combination in inhibiting the release of NO by the activated microglia: in fact, 10 μM PS combined with 5 μM curcumin inhibits 50% of the NO release into the culture medium, whereas a single treatment of 10 μM PS does not exceed 10%, and a single treatment of 5 μM curcumin causes less than 20% inhibition.

The synergic effect is due (at least partly) to the stabilisation of PS.

EXAMPLE 4

Bioavailability of PS/Curcumin Combinations

The bioavailability of curcumin was determined after oral administration of formulations containing *Curcuma longa* extract combined with phospholipids in various ratios. The phospholipids used are phosphatidylserine (PS) and phosphatidylcholine (PC), which are commonly employed commercially to increase the absorption of curcumin.

The comparison was performed vs. i.v. administration of turmeric alone.

Formulations and Doses

The formulations were prepared as follows

| | |
|---|---|
| i.v. treatment (T1): 3 mg/kg | Turmeric (10% DMSO, 5% solution in H$_2$O): 2 ml/kg |
| Oral treatment (T2): 340 mg/kg | Turmeric/PS liposomes-1:4 w/w, phosphate buffer pH 7.4: 10 ml/kg |
| Oral treatment (T3): 340 mg/kg | Turmeric/PS/PC liposomes-1:2:2 w/w/w phosphate buffer pH 7.4; 10 ml/kg |

Formulations T2 and T3 were prepared by dissolving turmeric in ethanol (500 mg turmeric/75 mL EtOH), heating the solutions to 60° C. and adding the phospholipids to the resulting solution. The solution was then placed under stirring for 3 hours, to induce the formation of liposomes. The solvent was extracted under vacuum. The formulations were prepared before each treatment by resuspending the mixture of liposomes in phosphate buffer pH 7.4 (14.7 mL).

Animals and Treatment

Sprague-Dawley rats (body weight 225-250 g) were used. All the animals were weighed on each day of treatment and monitored at regular intervals to identify any reactions to the treatment. Each animal was identified by a colour sprayed onto its back before the experiment. At the end of the experiment the animals were sacrificed after anaesthesia by i.v. overdose of sodium pentothal, Intervet. The experiment was conducted in compliance with the applicable Italian legislation (Legislative Decree 116/92).

Blood Samples i.v. treatment (T1): blood samples were taken from the caudal vein after 3, 10, 20, 60, 90, 120, 180 and 360 min.

Oral treatments (T2-T3): blood samples were taken from the caudal vein after 10, 30, 60, 90, 120, 180, 360, and 480 min.

Pharmacokinetic Analysis

Figure 3:
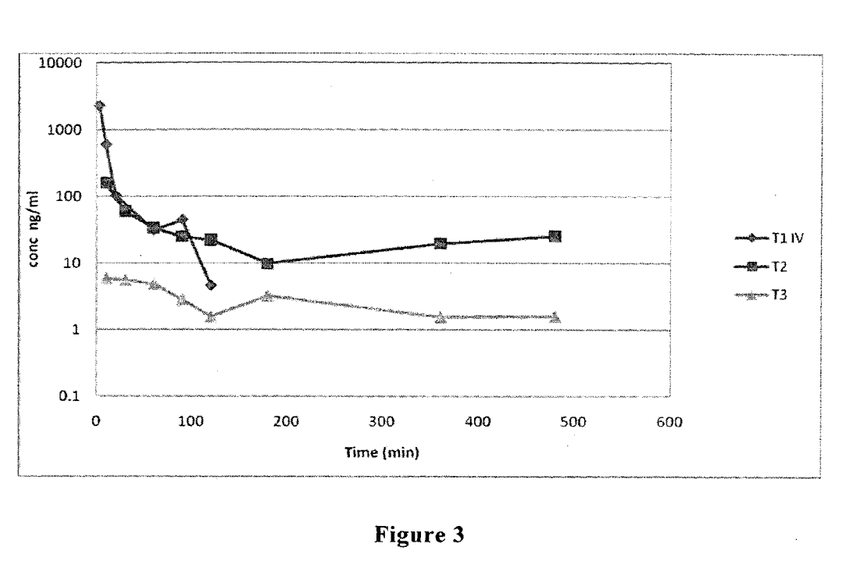
FIG. 3 is a graph indicating the bioavailability of three formulations after administration.

The following parameters were considered for each subject:

$C_{max}$ Maximum plasma concentration $C_{max}/D$ Maximum plasma concentration normalised to dose (FIG. 3)

$t_{max}$ Time taken to reach maximum plasma concentration

Results and Conclusions

The bioavailability of curcumin was evaluated by comparing the formulations in liposomes of PS or PC/PS in various ratios with i.v. administration. As expected, the absolute bioavailability proved very low in general, due to the liver metabolism (for example, due to formation of conjugates).

The data analysis presented in FIG. 3 clearly indicates that formulation T2 has excellent bioavailability which, shortly after administration, is actually comparable with that of i.v. treatment. The plasma concentration remains high, stable and constant for a long time, thus making it possible to reduce the number of daily administrations. Formulation T3, however, induces much lower blood levels.

It is clear that phosphatidylserine has an effect that strongly promotes the absorption of turmeric, to a far greater extent than phosphatidylcholine.

In fact, as the total turmeric:phospholipid ratio is 1:4 in both oral formulations, the improvement in the bioavailability of formulation T2 evidently depends not only on the mere presence of phospholipids, which are well known to be used for this purpose, but also on the nature of the phospholipid used.

EXAMPLE 5

PS/Curcumin: Synergic Inhibition of Release of IL-10

The experiment was conducted in two steps, and was designed to evaluate the effect on in vitro release of IL-1β from microglia BV-2 cells stimulated with LPS after administration of PS and curcumin. IL-1β is a cytokine strongly involved in the inflammatory processes underlying both osteoarticular disorders and neurodegeneration.

Materials and Methods

Murine microglial BV-2 cells were stimulated as described in Example 3 (0.1 µg/ml LPS for 16 hours) and then treated with PS and curcumin at the concentration of 1 µM or 5 µM. The IL-1β levels were determined by ELISA assay. The control (CTRL) was represented by cells stimulated with LPS but not treated.

Figure 4:
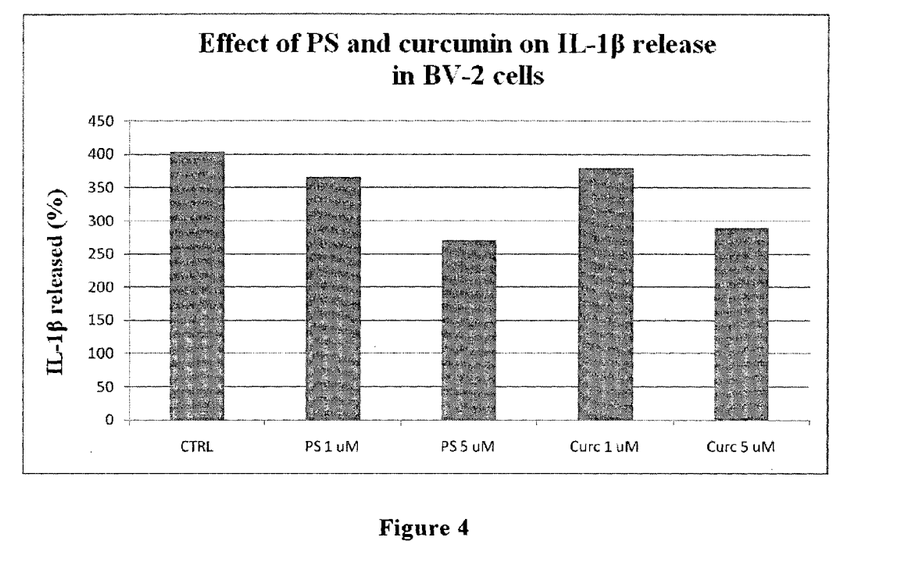
FIG. 4 is a graph showing the effect of PS and curcumin on IL-1β release in BV-2 cells.

FIG. 4 clearly shows that neither PS nor curcumin, administered individually, significantly inhibits the release of IL-1β from BV-2 cells stimulated with LPS; a limited effect occurs at the higher concentrations (5 µM) for both substances.

At the second stage of the experiment the effects of the combination of the two substances were evaluated on the same parameter according to the same protocol. To demonstrate the synergy, it was decided to combine the concentrations that produced the lowest inhibiting effect when individually administered.

Figure 5:
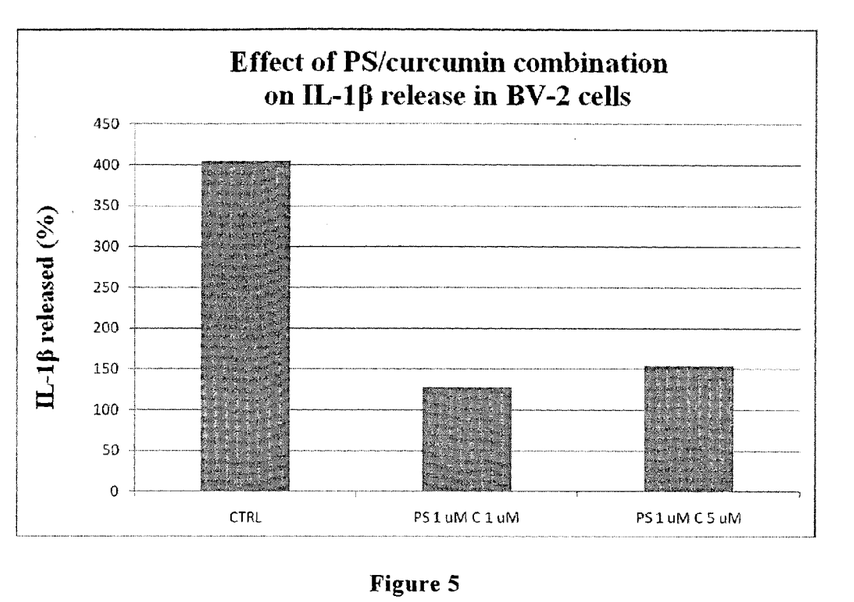
FIG. 5 is a graph showing the effect of PS/curcumin combination on IL-1β release in BV-2 cells.

The results are shown in FIG. 5.

The PS/curcumin combination significantly and synergically inhibits the release of IL-1β; the synergy is even more evident in view of the fact that the best inhibition was obtained with the concentrations that gave the worst results in the first part of the experiment (1 µM PS+1 µM curcumin).

EXAMPLE 6

PS/Curcumin: Increased Release of βIII Tubulin

The purpose of the experiment was to test the modulatory role of PS and curcumin on the effects of the neuroinflammatory processes that strongly inhibit neuronal differentiation by evaluating the expression of the protein βIII tubulin, an indicator for differentiation.

Materials and Methods

The experiment was conducted in compliance with the applicable Italian legislation.

Cultures of stem cells/neural progenitor cells (NPCs) obtained from the subventricular zone of adult mice were used. The NPCs were cultured under conditions of differentiation by mechanical dissociation of the neurospheres and seeding of the individual cells on plates coated with poly-ornithine and laminin in a culture medium only containing factor bFGF, according to state-of-the-art techniques.

The NPC cultures thus obtained were divided into aliquots, each of which was treated differently, as follows:

a) exposure to the culture medium of microglial cells activated with LPS, to induce inflammatory damage that prevents or strongly inhibits differentiation;

b) treatment a) and PS and curcumin administered separately at different concentrations;

c) treatment a) and PS/curcumin combined at different relative concentrations.

The control was represented by untreated NPC cells.

Neuronal differentiation was evaluated after 6 days, by immunocytochemical analysis with antibodies directed against the specific marker βIII tubulin, extrapolating the % concentration of protein present in the medium.

Figure 6:
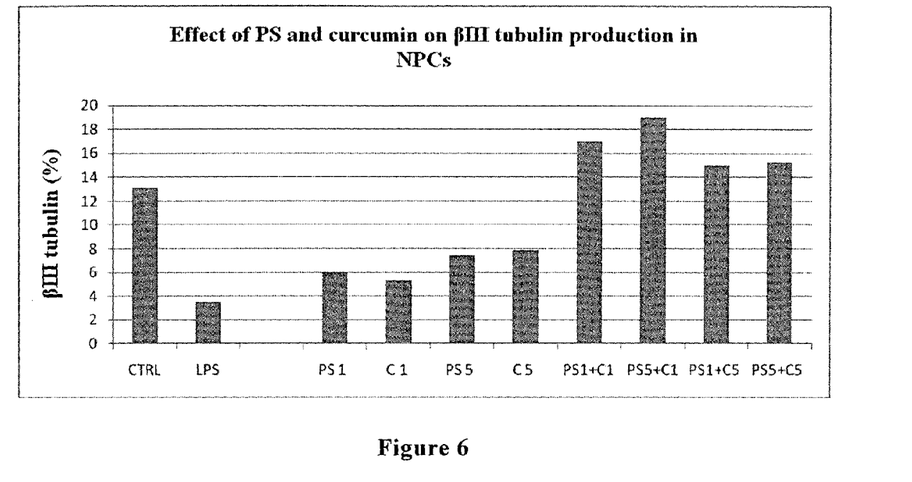
FIG. 6 is a graph presenting the effect of PS and curcumin on βIII tubulin production in NPCs.

The results are presented in FIG. 6. The concentrations are expressed in μM.

As expected in view of their known properties, in the presence of liposomes of PS alone (1 and 5 μM) and curcumin alone (1 and 5 μM), the percentage of cells positive to βIII tubulin was already slightly elevated at the lowest concentration for both substances, but did not differ significantly from that observed in the presence of LPS alone. Surprisingly, however, the PS/curcumin combination entirely cancelled out the inhibition of neuronal differentiation induced by LPS, restoring it to the control values as from the lowest concentrations used.

These latter results demonstrate that the combination of PS and curcumin liposomes has an undeniable synergic effect in restoring neuronal differentiation reduced under neuroinflammation conditions, unlike the two substances used separately.

In conclusion, in the present invention the Applicant has demonstrated:

that the pharmaceutical compositions containing the novel stable PS/curcumin combination described here have very high bioavailability after oral administration;

that the novel stable PS/curcumin combination has a synergic effect in reducing nitric oxide (NO) production;

that the novel stable PS/curcumin combination has a synergic effect in reducing the release of IL-1β, a cytokine strongly involved in inflammatory processes;

that the novel stable PS/curcumin combination has a synergic effect in promoting neuronal differentiation in cells subjected to neuroinflammatory stimulation;

and consequently describes and claims the use of the pharmaceutical compositions containing said combination in the prevention of the disorders associated with brain aging described above, and in the prevention and treatment of osteoporosis and/or osteoarthritis.

The invention claimed is:

1. A pharmaceutical composition or supplement comprising:

phosphatidylserine or a salt thereof and curcumin, wherein the phosphatidylserine is in the form of sodium salt and in a quantity ranging between 50 and 400 mg per dose, and the curcumin is present in a quantity ranging between 50 and 1000 mg per dose, the composition or supplement being devoid of degradation products.

2. The pharmaceutical composition or supplement as claimed in claim 1, wherein the phosphatidylserine is present in a quantity ranging between 100 and 200 mg per dose, and the curcumin is present in a quantity ranging between 100 and 600 mg per dose.

3. The pharmaceutical composition or supplement as claimed in claim 1, wherein the phosphatidylserine is produced in a biphasic system formed by an aqueous solution and an organic solvent in the presence of calcium oxide.

4. The pharmaceutical composition or supplement as claimed in claim 1, also containing one or more lipid excipients, triglycerides and/or phospholipids, and/or surfactants, and/or adsorbing agents, and/or preservative/antioxidant agents, and/or pH regulators.

5. The pharmaceutical composition or supplement as claimed in claim 1, also containing one or more pharmacologically and/or biologically active agents of natural and/or synthetic origin.

6. The pharmaceutical composition or supplement as claimed in claim 1 in the form of a soft capsule, a sachet, a tablet, a bar, a solution or a dispersion.

7. A method for the treatment of a neurodegenerative disorder with cognitive deficit and memory alteration is Alzheimer's disease, senile or pre-senile dementia or vascular dementia which comprises administering to a patient in need thereof a pharmaceutical composition or supplement according to claim 1.

8. A method for the treatment of primary and secondary osteoporosis which comprises administering to a patient in need thereof a pharmaceutical composition or supplement according to claim 1.

9. A method for the treatment of osteoarthritis which comprises administering to a patient in need thereof a pharmaceutical composition or supplement according to claim 1.

10. A method for stabilizing pharmaceutical compositions or supplements containing phosphatidylserine against chemical or enzymatic degradation processes which comprises incorporating curcumin in a pharmaceutical composition or supplement containing phosphatidylserine.

11. The pharmaceutical composition or supplement as claimed in claim 5, wherein said pharmacologically and/or biologically active agent is at least one member selected from the group consisting of vitamins, minerals salts, tonic agents, anti-inflammatories and aminoacids.

12. The method according to claim 10, wherein the phosphatidylserine is in the form of sodium salt and in a quantity ranging between 50 and 400 mg per dose, and the curcumin is present in a quantity ranging between 50 and 1000 mg per dose, the composition or supplement being devoid of degradation products.

13. The method according to claim 10, wherein the phosphatidylserine is present in a quantity ranging between 100 and 200 mg per dose, and the curcumin is present in a quantity ranging between 100 and 600 mg per dose.

14. The method according to claim 10, wherein the phosphatidylserine is produced in a biphasic system formed by an aqueous solution and an organic solvent in the presence of calcium oxide.

15. The method according to claim 10, wherein the pharmaceutical composition or supplement also contains one or more lipid excipients, triglycerides and/or phospholipids, and/or surfactants, and/or adsorbing agents, and/or preservative/antioxidant agents, and/or pH regulators.

16. The method according to claim 10, wherein the pharmaceutical composition or supplement also contains one or more pharmacologically and/or biologically active agents of natural and/or synthetic origin.

17. The method according to claim 16, wherein said pharmacologically and/or biologically active agent is at least one member selected from the group consisting of vitamins, minerals salts, tonic agents, anti-inflammatories and aminoacids.

18. The method according to claim 10, wherein the pharmaceutical composition or supplement is in the form of a soft capsule, a sachet, a tablet, a bar, a solution or a dispersion.

19. A method for the treatment of a neurodegenerative disorder with cognitive deficit and memory alteration is Alzheimer's disease, senile or pre-senile dementia or vascular dementia which comprises administering to a patient in need thereof a pharmaceutical composition or supplement stabilized according to the method of claim 10.

20. A method for the treatment of primary and secondary osteoporosis which comprises administering to a patient in need thereof a pharmaceutical composition or supplement stabilized according to the method of claim 10.

21. A method for the treatment of osteoarthritis which comprises administering to a patient in need thereof a pharmaceutical composition or supplement stabilized according to the method of claim 10.

22. A method for the treatment of a neurodegenerative disorder with cognitive deficit and memory alteration is Alzheimer's disease, senile or pre-senile dementia or vascular dementia which comprises administering to a patient in need thereof a pharmaceutical composition or supplement comprising phosphatidylserine or a salt thereof and curcumin.

23. A method for the treatment of primary and secondary osteoporosis which comprises administering to a patient in need thereof a pharmaceutical composition or supplement comprising phosphatidylserine or a salt thereof and curcumin.

24. A method for the treatment of osteoarthritis which comprises administering to a patient in need thereof a pharmaceutical composition or supplement comprising phosphatidylserine or a salt thereof and curcumin.

25. The method according to claim 22, wherein the pharmaceutical composition or supplement also contains one or more lipid excipients, triglycerides and/or phospholipids, and/or surfactants, and/or adsorbing agents, and/or preservative/antioxidant agents, and/or pH regulators.

26. The method according to claim 22, wherein the pharmaceutical composition or supplement also contains one or more pharmacologically and/or biologically active agents of natural and/or synthetic origin.

27. The method according to claim 26, wherein said pharmacologically and/or biologically active agent is at least one member selected from the group consisting of vitamins, minerals salts, tonic agents, anti-inflammatories and aminoacids.

28. The method according to claim 22, wherein the pharmaceutical composition or supplement is in the form of a soft capsule, a sachet, a tablet, a bar, a solution or a dispersion.

29. The method according to claim 23, wherein the pharmaceutical composition or supplement also contains one or more lipid excipients, triglycerides and/or phospholipids, and/or surfactants, and/or adsorbing agents, and/or preservative/antioxidant agents, and/or pH regulators.

30. The method according to claim 23, wherein the pharmaceutical composition or supplement also contains one or more pharmacologically and/or biologically active agents of natural and/or synthetic origin.

31. The method according to claim 30, wherein said pharmacologically and/or biologically active agent is at least one member selected from the group consisting of vitamins, minerals salts, tonic agents, anti-inflammatories and aminoacids.

32. The method according to claim 23, wherein the pharmaceutical composition or supplement is in the form of a soft capsule, a sachet, a tablet, a bar, a solution or a dispersion.

33. The method according to claim 24, wherein the pharmaceutical composition or supplement also contains one or more lipid excipients, triglycerides and/or phospholipids, and/or surfactants, and/or adsorbing agents, and/or preservative/antioxidant agents, and/or pH regulators.

34. The method according to claim 24, wherein the pharmaceutical composition or supplement also contains one or more pharmacologically and/or biologically active agents of natural and/or synthetic origin.

35. The method according to claim 34, wherein said pharmacologically and/or biologically active agent is at least one member selected from the group consisting of vitamins, minerals salts, tonic agents, anti-inflammatories and aminoacids.

36. The method according to claim 24, wherein the pharmaceutical composition or supplement is in the form of a soft capsule, a sachet, a tablet, a bar, a solution or a dispersion.

* * * * *